(12) United States Patent
Everett et al.

(10) Patent No.: US 8,115,935 B2
(45) Date of Patent: *Feb. 14, 2012

(54) METHOD OF MOTION CORRECTION IN OPTICAL COHERENCE TOMOGRAPHY IMAGING

(75) Inventors: Matthew J. Everett, Livermore, CA (US); Keith E. O'Hara, San Ramon, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,926

(22) Filed: Jun. 7, 2010

(65) Prior Publication Data

US 2010/0245838 A1    Sep. 30, 2010

Related U.S. Application Data

(63) Continuation of application No. 12/075,477, filed on Mar. 11, 2008, now Pat. No. 7,755,769, which is a continuation of application No. 11/331,567, filed on Jan. 13, 2006, now Pat. No. 7,365,856.

(60) Provisional application No. 60/645,637, filed on Jan. 21, 2005.

(51) Int. Cl.
*G01B 11/02* (2006.01)

(52) U.S. Cl. ........................................ 356/497

(58) Field of Classification Search .................. 356/479, 356/497; 250/227.19, 227.27
See application file for complete search history.

(56) References Cited

U.S. PATENT DOCUMENTS 4,937,526 A    6/1990 Ehman et al.
(Continued)

FOREIGN PATENT DOCUMENTS

WO    WO 03/105678 A2    12/2003
(Continued)

OTHER PUBLICATIONS

R.L. Ehman et al., "Adaptive Technique for High-Definition MR Imaging of Moving Structures," *Radiology*, vol. 173, No. 1, (1989), pp. 255-263.

(Continued)

*Primary Examiner* — Gregory J Toatley
*Assistant Examiner* — Scott M Richey
(74) *Attorney, Agent, or Firm* — Morrison & Foerster LLP

(57) ABSTRACT

An image data set acquired by an optical coherence tomography (OCT) system is corrected for effects due to motion of the sample. A first set of A-scans is acquired within a time short enough to avoid any significant motion of the sample. A second more extensive set of A-scans is acquired over an overlapping region on the sample. Significant sample motion may occur during acquisition of the second set. A-scans from the first set are matched with A-scans from the second set, based on similarity between the longitudinal optical scattering profiles they contain. Such matched pairs of A-scans are likely to correspond to the same region in the sample. Comparison of the OCT scanner coordinates that produced each A-scan in a matching pair, in conjunction with any shift in the longitudinal scattering profiles between the pair of A-scans, reveals the displacement of the sample between acquisition of the first and second A-scans in the pair. Estimates of the sample displacement are used to correct the transverse and longitudinal coordinates of the A-scans in the second set, to form a motion-corrected OCT data set.

35 Claims, 4 Drawing Sheets

U.S. PATENT DOCUMENTS

| | | | | |
|---|---|---|---|---|
| 5,471,303 A | * | 11/1995 | Ai et al. | 356/497 |
| 5,644,642 A | | 7/1997 | Kirschbaum | |
| 6,325,512 B1 | | 12/2001 | Wei | |
| 6,501,551 B1 | * | 12/2002 | Tearney et al. | 356/477 |
| 6,552,796 B2 | * | 4/2003 | Magnin et al. | 356/450 |
| 6,556,853 B1 | * | 4/2003 | Cabib et al. | 600/407 |
| 6,726,325 B2 | | 4/2004 | Xie et al. | |
| 6,736,508 B2 | * | 5/2004 | Xie et al. | 351/209 |
| 6,769,769 B2 | | 8/2004 | Podoleanu et al. | |
| 6,788,421 B2 | * | 9/2004 | Fercher et al. | 356/497 |
| 6,927,860 B2 | | 8/2005 | Podoleanu et al. | |
| 7,072,047 B2 | | 7/2006 | Westphal et al. | |
| 7,113,818 B2 | * | 9/2006 | Podoleanu et al. | 600/476 |
| 7,133,137 B2 | * | 11/2006 | Shimmick | 356/497 |
| 7,145,661 B2 | * | 12/2006 | Hitzenberger | 356/497 |
| 7,365,856 B2 | * | 4/2008 | Everett et al. | 356/497 |
| 7,512,436 B2 | * | 3/2009 | Petty et al. | 600/476 |
| 7,755,769 B2 | * | 7/2010 | Everett et al. | 356/497 |
| 8,018,598 B2 | * | 9/2011 | Cense et al. | 356/456 |
| 2002/0085208 A1 | * | 7/2002 | Hauger et al. | 356/479 |
| 2003/0103212 A1 | | 6/2003 | Westphal et al. | |
| 2003/0199769 A1 | | 10/2003 | Podoleanu et al. | |
| 2003/0227631 A1 | | 12/2003 | Rollins et al. | |
| 2005/0140984 A1 | | 6/2005 | Hitzenberger | |
| 2005/0219544 A1 | * | 10/2005 | Chan et al. | 356/497 |
| 2006/0228011 A1 | * | 10/2006 | Everett et al. | 382/128 |

FOREIGN PATENT DOCUMENTS

| | | |
|---|---|---|
| WO | WO 2004/055473 A1 | 7/2004 |

OTHER PUBLICATIONS

D.X. Hammer et al., "Active retinal tracker for clinocal optical coherence tomography sytems" *Journal of Biomedical Optics*, vol. 10, No. 2, Mar./Apr. 2005, pp. 024038-1-024038-11.

T.M. Joergensen et al., "Reducing speckle noise on retinal OCT images by aligning multiple B-scan," Coherence Domain Optical Methods and Optical Coherence Tomography in Biomedicine VIII (Bellingham, WA), *Proceedings of SPIE*, vol. 5316, (2004), pp. 205-213.

C.K. Hitzenberger et al., "Three-dimensional imaging of the human retina by high-speed optical coherence tomography," *Optics Express*, vol. 11, No. 21, Oct. 20, 2003, pp. 2753-2761.

D. Huang, et al., "Optical Coherence Tomography," *Science*, vol. 254, No. 5035, Nov. 22, 1991, pp. 1178-1181.

De Boer et al., "Improved signal-to-noise ratio in spectral-domain compared with time-domain optical coherence tornoqraphy," Optics Letters, vol. 28, No. 21, Nov. 1, 2003, pp. 2067-2069.

Choma et al., "Sensitivity advantage of swept source and Fourier domain optical coherence tomography," Optics Express, vol. 11, No. 18, Sep. 8, 2003, pp. 2183-2189.

Leitgeb et al., "Performance of fourier domain vs. time domain optical coherence tomography," Optics Express, vol. 11, No. 8, Apr. 21, 2003, pp. 889-894.

Nassif et al., "In vivo high-resolution video-rate spectral-domain optial coherence tomography of the human retina and optic nerve", Optics Express, vol. 12, No. 3, Feb. 9, 2004, pp. 367-376.

\* cited by examiner

METHOD OF MOTION CORRECTION IN OPTICAL COHERENCE TOMOGRAPHY IMAGING

PRIORITY

This application is a continuation of U.S. patent application Ser. No. 12/075,477, filed Mar. 11, 2008, which in turn is a continuation of U.S. patent application Ser. No. 11/331,567, filed Jan. 13, 2006 (now U.S. Pat. No. 7,365,856), which in turn claims the benefit of the filing date under 35 U.S.C. §119(e) of U.S. Provisional Patent Application Ser. No. 60/645,637, filed Jan. 21, 2005, which are hereby incorporated herein by reference in its entirety.

TECHNICAL FIELD OF THE INVENTION

The present invention relates to data acquisition methods for imaging by optical coherence tomography (OCT). In particular, the invention is a method for determining patient motion occurring during the acquisition of large sets of data by OCT. The method described herein acquires a sparse set of OCT data in a sufficiently short time that patient motion during the acquisition is not objectionable. The sparse set of OCT data acts as a set of guideposts for determination of the locations on the sample, of the measurements comprising the full data set.

BACKGROUND OF THE INVENTION

Optical Coherence Tomography (OCT) is a technique for performing high-resolution cross-sectional imaging that can provide images of tissue structure on the micron scale in situ and in real time [Huang et al. (1991)]. OCT is a method of interferometry that determines the scattering profile of a sample along the OCT beam. Each scattering profile is called an axial scan, or A-scan. Cross-sectional images, and by extension 3D volumes, are built up from many A-scans, with the OCT beam moved to a set of transverse locations on the sample. Motion of the sample with respect to the OCT scanner will cause the actual locations measured on the sample to be arranged differently than the scan pattern in scanner coordinates, unless the motion is detected and the OCT beam placement corrected to track the motion.

In recent years, frequency domain OCT techniques have been applied to living samples [Nassif et al. (2004)]. The frequency domain techniques have significant advantages in speed and signal-to-noise ratio as compared to time domain OCT [Leitgeb, R. A., et al., (2003); de Boer, J. F. et al., (2003); Choma, M. A., et al. (2003)]. The greater speed of modern OCT systems allows the acquisition of larger data sets, including 3D volume images of human tissue.

In the case of ophthalmology, a typical patient can comfortably hold his eye open for a few seconds. OCT systems can advantageously use these few seconds to collect extensive images. During such an acquisition, motion of the patients head and natural shifts in the patient's fixation will distort the image. Tracking the motion of the eye to correct the placement of the OCT beam has proven useful [U.S. Pat. No. 6,736,508; Hammer, D. X., et al. (2005)]. There is also motion along the OCT beam, which is not detectable by the common designs of eye trackers, but which does distort the OCT image.

There is therefore a need for a method to correct the placement of OCT image data acquired on a moving sample. The correction could be applied to the mechanism scanning the OCT beam, to approximately follow the motion of the sample. Alternatively, the correction could be applied when images are built from the A-scans acquired in the presence of sample motion. The need is for a method to determine the motion, in three dimensions, of the sample during the acquisition of the A-scans. A method that does not require an additional optical system for eye tracking would have the advantages of simplicity and lower cost.

SUMMARY OF THE INVENTION

The present invention acquires, in addition to the set of A-scans comprising the desired image, a widely-spaced set of guidepost A-scans that can be recorded quickly enough to avoid objectionable motion of the sample. This method compares some of the A-scans comprising the image with some of the guidepost A-scans. When comparison shows that the optical scattering profile of an image A-scan and guidepost A-scan closely match, the location of the image A-scan on the moving sample is assumed to be the same as that of the matching guidepost A-scan.

If one were to assume no sample motion, one would expect the matches to be found during the course of the imaging scan pattern, whenever the OCT beam probes the same location, with respect to the scanner, as it did when collecting one of the guideposts (i.e. the scanner coordinates of the OCT system would be the same). Motion of the sample will cause the matches to occur for A-scans recorded at somewhat different scanner coordinates than would have been expected under the assumption of no sample motion. Each time a match is found, comparison of the actual scanner coordinates and the expected scanner coordinates (under the assumption of no sample motion), reveals the transverse displacement of the sample between acquisition of the guidepost scans and the acquisition of the matching A-scan in the image set. Comparison of the contents of the matching pair of A-scans reveals any longitudinal displacement of the sample, which would appear as a longitudinal shift in the image data between the matching pair of A-scans.

The comparison between A-scans need only be done between pairs of A-scans that are likely to match, such as those pairs which would have measured nearly the same location on the sample in the absence of sample motion. Depending on the comparison method, many pairs may match to some degree, so the method chooses the best-matching pair.

During the course of the imaging scan pattern, each match found provides updated information on the displacement of the sample. One can estimate the position of the sample between such matches by fitting a smooth curve through the points determined by the matches. Given the resulting curve of sample position versus time, the image data can be shifted to its correct locations, to form a 3D image free of motion artifact.

Other methods of determining eye motion use a landmark, such as the optic disk. The landmark is identified first, and its location is monitored as the detailed OCT scan proceeds. The landmark can be tracked on a separate imaging system, or the OCT beam can scan the landmark occasionally, briefly interrupting the larger data acquisition. However, good landmarks are not always found in diseased tissue. The method disclosed here takes advantage of the fact that the details in the structure of any tissue can serve the same need as a landmark.

DETAILED DESCRIPTION OF THE PREFERRED EMBODIMENT

Figure 1:
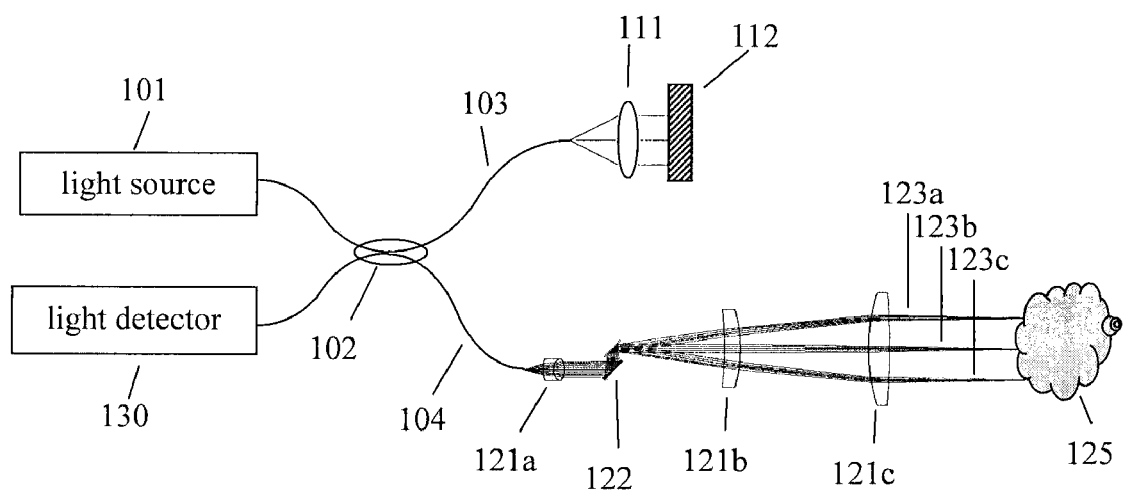
FIG. 1 illustrates schematically one type of OCT system.

FIG. 1 is a schematic illustration of one design of OCT system. The light source 101 provides light having a short-coherence length to the fiber-based interferometer. Directional coupler 102 serves to split the light from source 101 between a reference arm 103 and a sample arm 104. Lens 111 and mirror 112 serve to return reference light back to coupler 102. A scanning system including lenses 121a, 121b, and 121c, and scanning mirrors 122, directs light successively along paths such as 123a, 123b, 123c onto successive locations on sample 125. Some light scattered from sample 125 returns closely enough along the illumination path to re-enter the fiber interferometer, is combined with reference light in coupler 102. The interfered sample and reference light are detected in detector 130.

The scanning mirror 122 is controlled by a system processor and generates scan coordinates which correspond to certain transverse positions on the sample. A sample, such as the human eye, will move with respect to the OCT system. Once the sample moves the scanner coordinates associated with a particular transverse position on the sample will change in an unknown manner. The subject application describes a method for determining the extent of this displacement and correcting for that displacement.

As noted above, the sample 125 may move with respect to the measurement system causing a time-dependent difference between scanner coordinates and sample coordinates. In some OCT systems, such as handheld scanners, motion of the scanning optics can contribute to the relative motion between scanner coordinates and sample coordinates.

Figure 2:
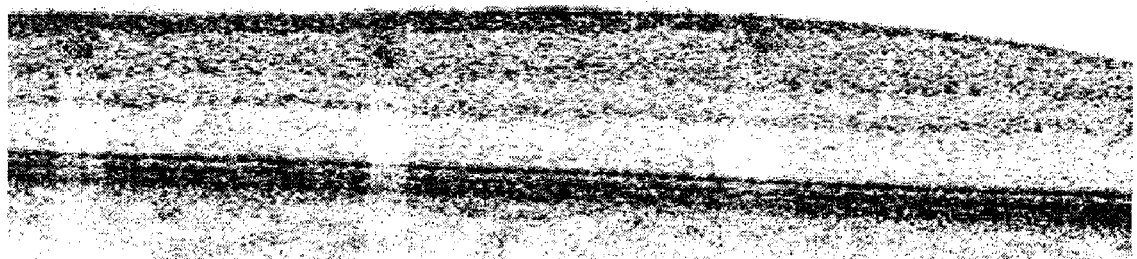
FIG. 2 is an example of an OCT image of human eye tissue, showing the detail that exists within the image.

FIG. 2 shows an example OCT tomogram from human tissue. Each column in this image is one A-scan; successive A-scans at neighboring locations in tissue are placed side-by-side to form the image. The grey scale is inverted, with highly scattering regions shown dark, to better reproduce the structure within the image that this method uses to recognize regions of tissue.

Figure 3:
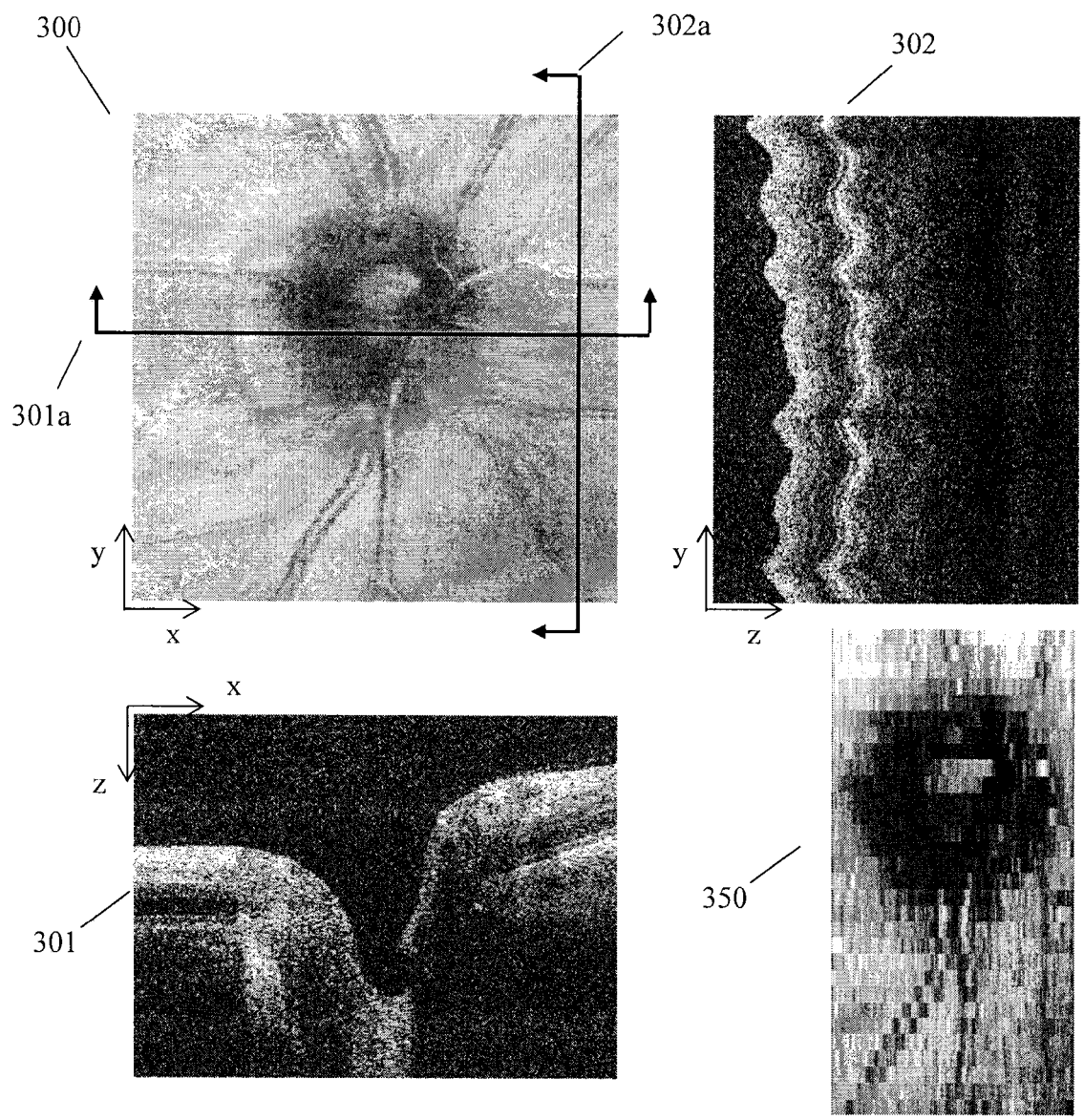
FIG. 3 shows three views of a 3D OCT data set collected from a human eye, in which motion artifact is visible.

Referring to FIG. 3, a three dimensional data set acquired from a human eye is shown in three views. En-face projection 300 is the integrated optical scattering, integrated along depth z to produce a view similar to what one would see in an ophthalmoscope. Sections 301 and 302 show sections of the volume in which one axis z is the direction of propagation of the OCT beam. Section indicators 301a and 302a show the locations of sections 301 and 302, respectively, in projection 300. Sections such as 301 and 302 are called tomograms. The columns comprising tomogram 301, and the rows comprising tomogram 302, are individual A-scans. Each pixel in the projection 300 is the integrated intensity from one A-scan. The dimensions of the tissue within the image are approximately 3 mm along each of x and y, 1.5 mm along z.

The acquisition of A-scans for this example proceeded along the horizontal rows of projection 300. Tomogram 301 is one of these rows, so the A-scans comprising this section were acquired sequentially. Tomogram 302 consists of A-scans chosen from successive rows, so one sees in section 302 the motion of the sample during the duration of the acquisition of the full 3D volume.

In addition to the raster of A-scans, we acquire a set of guidepost A-scans, which is represented in FIG. 3 by the lower-resolution en-face image 350 composed of the integrated optical scattering in the set of guidepost A-scans en-face image. The preferred embodiment uses approximately a 32-by-32 grid of guidepost A-scans, which can be acquired within 100 milliseconds by modern OCT techniques. For purposes of illustration, the example of FIG. 3 uses a guidepost set consisting of 30 rows of 128 A-scans; this larger set produces a more recognizable en-face image 350, while still requiring less than 200 milliseconds for acquisition by modern OCT techniques.

The set of guidepost A-scans is preferably acquired quickly enough that the sample is substantially stationary, meaning that there is no objectionable motion of the sample. For example, when imaging the retina of the human eye, the transverse optical resolution is typically no better than 5 microns. The fast motions of the eye called tremor cause only a few microns apparent motion of the retina, apparent motions being the motion as seen through the optics of the human eye. Motions due to tremor are typically not resolvable, so they are not considered objectionable. The jerk-like eye rotations called saccades can cause 100 microns apparent motion, so they are objectionable. Saccades occur irregularly, approximately once per second. Thus when applied to OCT of the human eye, the set of guidepost A-scans must be acquired within significantly less than one second in order to avoid objectionable motion. Acquisition of the guidepost A-scans within 200 milliseconds is preferred in this application.

For comparison purposes, the full raster scan of image information shown in FIG. 3 corresponds to 256 rows of 256 A-scans. Using current technology, this raster scan can take on the order of 1 to 2 seconds to perform during which time the eye will move.

There are alternatives to a raster scan for collecting the OCT imaging information. One can use a set of radial scans, scanning transversely across a set of lines that extend outward from a center point; radial scans in this pattern have the characteristic of higher density sampling near the crossing point. Another alternative pattern is a set of concentric circles. Because the currently described method takes advantage of revisiting the portions of the sample seen during collection of a set of guideposts, the method provides the greatest advantage when the scan pattern for the full data set covers a two-dimensional area. Scan patterns with a two-dimensional transverse extent can be collected using a scan pattern designed to frequently cross a set of guideposts, with the guideposts conveniently collected using one or a few transverse scan lines. A two-dimensional extent in this context is an area having transverse dimensions more than ten times the transverse optical resolution, so that meaningful tomogram images can be extracted in each transverse dimension, such as tomograms 301 and 302 in FIG. 3.

The guidepost A-scans are compared with A-scans in the raster for the purpose of finding matches of the scattering profile. One effective comparison method is the normalized cross-correlation, defined by $$X_{12}(t) \equiv \int a_1^*(z) \cdot a_2(z-t) dz \bigg/ \sqrt{\int a_1^2 dz \cdot \int a_2^2 dz}$$

where a(z) is a measure of the scattering intensity along the OCT beam, t is a variable indicating the relative shift along the beam direction of the two A-scans, and the * denotes complex conjugation. The A-scans $a_1$ and $a_2$ are chosen from the guidepost set and the raster, respectively.

If the A-scans were measured at locations more closely spaced than the width of the OCT beam, then there will likely be one A-scan in each row of the full data set which correlates well with one guidepost A-scan. If there has been eye motion in x and y between acquisition of the guideposts and acquisition of the raster scan, the pair of A-scans with the highest cross-correlation will consist of two A-scans acquired at different sets of scanner coordinates of the OCT system. The difference in scan coordinates reveals the transverse displacement of the sample between acquisition of the guideposts and acquisition of the matching A-scan in the raster.

The cross-correlation is a function of the shift t. The value of t at which $X_{12}(t)$ is maximized reveals the longitudinal displacement of the sample, along z, between acquisition of the guideposts and acquisition of the matching A-scan in the raster. In this way the displacement in x, y and z of the sample is determined at several points along the raster scan, each time a good match is found between an A-scan in the raster and an A-scan in the set of guideposts. The location of the sample between such matches is estimated by fitting a smooth curve, as a function of progress time of the raster scan, through the points determined by the matches. Given the resulting curve of sample displacement versus time, the data in the raster of A-scans can be shifted and interpolated to form a three-dimensional data set that is free of motion artifact.

The method disclosed herein is most effective when used to accurately correct minor movements during acquisition of the image A-scans. It can be advantageously combined with prior art methods that are better suited to correct sudden motions, such as saccades of the eye. One prior art method that is better suited to correction of saccades is cross-correlation of each tomogram in the image set of A-scans with its immediate neighbors; this prior art method relies on continuity of anatomical features between tomograms. The method disclosed herein could also be advantageously combined with coarse tracking of sample motion; coarse tracking may be more practical to implement than tracking accurate enough to eliminate all objectionable displacement between the desired and actual measurement locations.

Figure 4:
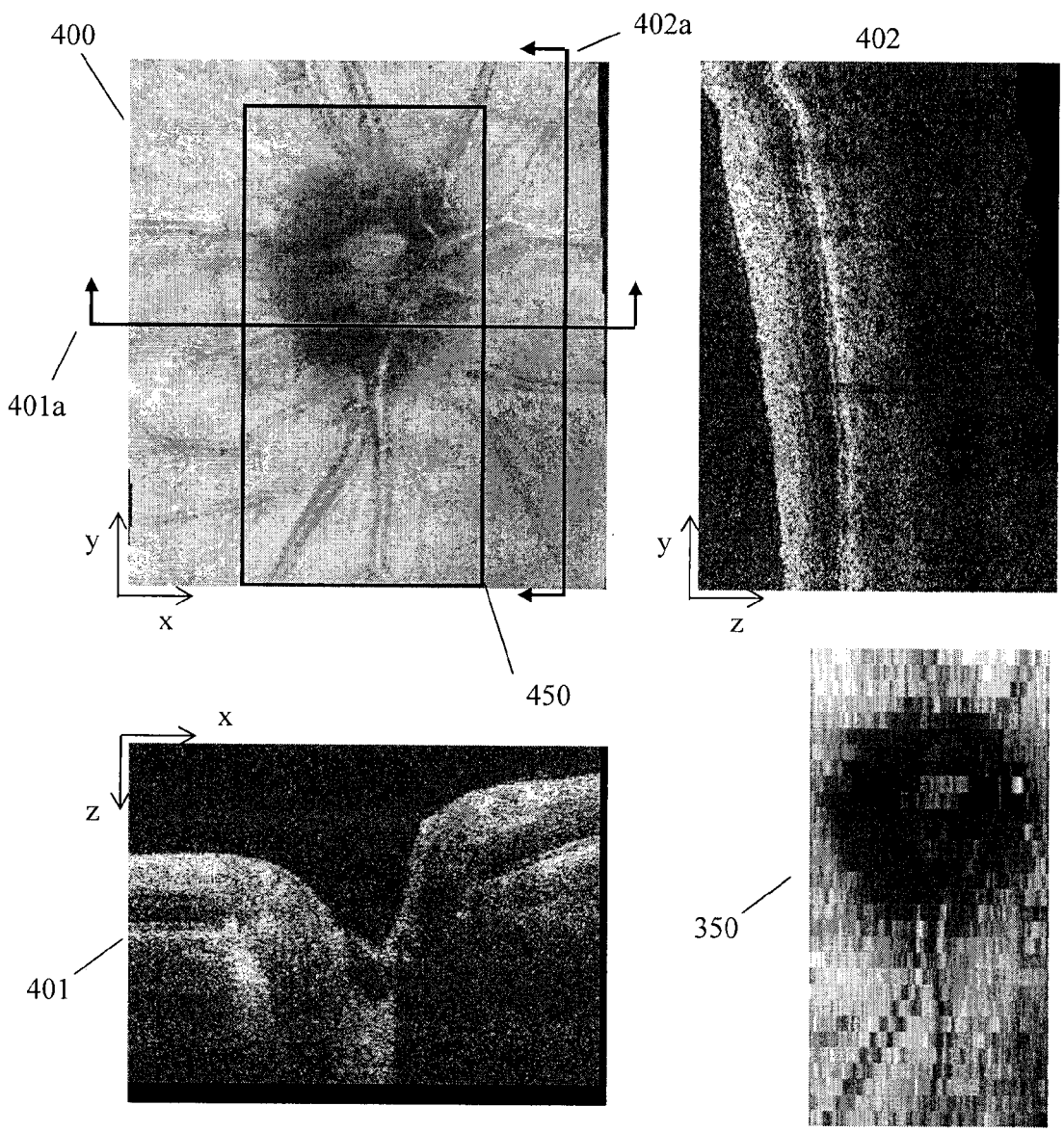
FIG. 4 shows three views of a 3D OCT data set collected from a human eye, in which motion artifact has been largely corrected by the methods disclosed herein.

FIG. 4 shows the data of FIG. 3 after correction using the method described herein. The data contained in the image A-scans has been shifted, and interpolated as necessary, so that each image A-scans that matched a guidepost A-scan now appears in a position corresponding to the location where that guidepost A-scan was acquired. En-face projection 400 is built from the optical scattering in this corrected data set, integrated along depth z. Tomograms 401 and 402 are sections through the corrected data set, related to projection 400 as indicated by section indicators 401a and 402a respectively. Indication 450 shows the location extent of the guidepost set 350 in relation to the full set of image A-scans.

The motion artifact seen in tomogram 302 is corrected in tomogram 402. Tomogram 402 represents the true shape of the imaged tissue section. Correction of the en-face projection 400 is more subtle, but can be noted by comparing it with en-face projections 300 and 350.

An alternative pattern for the set of guideposts would be to form one or more generally diagonal sections across the volume to be covered by the full data set. Then in the absence of motion, each row of A-scans in the raster will be likely to match one of the A-scans in each diagonal section. However, there can be occasional erroneous matches between A-scans acquired at two different locations in tissue, when the tissue at these two locations happens by chance to have similar optical scattering profiles. Such erroneous matches would cause distortion in the output. The grid pattern of guidepost A-scans used in the examples of FIG. 3 and FIG. 4 tends to provide clusters of matches to the image A-scans; that is, some rows in the raster contain several neighboring A-scans that have matching guidepost A-scans. Having matches occur in clusters, coupled with the knowledge that matches within a cluster should show nearly the same sample displacement due to their proximity in time, plus a step of fitting the displacements determined by the matches to a smooth curve in time, gives protection against erroneous matches. Patterns of guideposts that cause matches to occur in clusters are therefore preferred.

A number of practical complications can be accommodated in this method. There are some choices for the function a(z) used to represent each A-scan. In many methods of OCT, including the modern Fourier-domain methods, the information on the amplitude and phase of the scattered light is recorded; a(z) could be chosen to be this complex-valued function. However, between acquisition of the guidepost scans and acquisition of the corresponding A-scans in the raster, the relative phases of the light scattered from different depths may have changed. This will happen if scattering centers move relative to one another by even a fraction of a wavelength of the probe light. Such motion is likely in living tissue, and such changes in a(z) would prevent one from finding a good match. For this reason, a(z) is best taken to be the real-valued intensity of light scattered from depth z, so that the comparison ignores the phase information.

OCT typically measures the scattering with an axial resolution of a few microns. Motion of some tissues, such as blood vessels, can change the scattering profile over this length scale. Also, if the spacing of A-scans in the raster is not much less than the OCT beam diameter, then no A-scan in the raster will exactly match any guidepost A-scan. One can apply smoothing of the scattered intensity, as measured by OCT, and use the values in the smoothed data set to form the function a(z). The preferred amount of smoothing retains as much detail in the A-scans as can be expected to be found upon re-measuring the same tissue, given the motion within the tissue and the coarseness of the raster scan.

Failures to find well-correlated A-scans will still occur. Eye motion during acquisition of a row in the raster could cause a failure, if the eye motion causes the raster to skip over the region covered by one of the diagonal traces in the guidepost set. Intermittent failures in the scan, due to dust on optics or floaters in the eye, could make a few a-scans un-useable. Eye motion greater than the extent of the region scanned will also cause registration failures. If the comparison method is cross-correlation, failed matches are recognized by their low cross-correlation coefficient, relative to the coefficient found in non-moving similar tissue. The effect of failed matches is mitigated by the step fitting of a smooth curve through the displacements determined by successful matches. Failed matches can be omitted from the fit, or the cross-correlation coefficient can be used as a confidence value in weighted fitting.

We consider now efficient application of the preferred embodiment to Fourier-domain methods of OCT, which record interference spectra at each transverse location on the sample. It is desirable to have a method of finding the proper position of an A-scan quickly directly from the spectrum, without taking the Fourier transform required to reconstruct the A-scan. Calculating the displacement of the sample quickly is desired to allow correction of the raster scan position during the raster scan, so that areas are not skipped due to motion of the patient against the direction of the scan.

The cross-correlation $X_{12}$ can be efficiently calculated from the spectra that are directly provided in Fourier-domain methods of OCT. The cross-correlation between two A-scans is the Fourier transform of the product of the two corresponding fringe spectra (the portion of the spectra due to interference, after subtracting the intensity of the reference beam). Each A-scan is related to a fringe spectrum through $$a(z) = \int e^{i2qz} S(q) dq,$$

where S(q) is the fringe spectrum as a function of the optical frequency q, with q in units of radians of optical phase per unit length. The cross-correlation is related to the fringe spectra by $$X_{12}(t) \equiv \int e^{i2q \cdot t} S_1^*(q) \cdot S_2(q) dq \Big/ \sqrt{\int S_1^2 dz \cdot \int S_2^2 dz}.$$

The cross-correlation between a pair of A-scans, if the A-scans are recorded at the same transverse location on the patient to within the beam diameter, has a peak at a position corresponding to the motion along the z-axis between acquisition of the two A-scans. The size of these peaks will be greatest for the pair of A-scans that best overlap in the transverse directions. Thus, the integrated squared magnitude of the cross-correlation indicates quantitatively the goodness of match between a pair of A-scans, and this integrated magnitude is the same as the integrated squared magnitude of the point-by-point product of the corresponding spectra, by Parseval's theorem. The integrated squared magnitude of the cross-correlation is efficiently calculated from $$C_{12} = \int |X_{12}(z)|^2 dz \equiv \int |S_1(q) S_2^*(q)|^2 dq \Big/ \sqrt{\int S_1^2 dq \cdot \int S_2^2 dq}.$$

The quantity $C_{12}$, computed for each pair of A-scans that is a candidate match, is used to identify matching pairs and thus the sample displacement in x and y. Then the value of the shift t at which $X_{12}$ has its peak value is used to determine the sample displacement in z.

One further complication is that Fourier-domain OCT techniques that record a single interference spectrum for each A-scan, with a single-phase of the reference beam, produce a double image. Each A-scan a(z) consists of the reflectivity profile along z, plus the mirror image of that profile. The cross-correlation is complicated by this mirror image, having two peaks instead of one: a peak at the position corresponding to the z-motion of the patient between acquisitions and another peak at the position corresponding to the negative of the z-motion of the patient.

One can avoid this problem by eliminating the part of the A-scan corresponding to positions z<0. Working directly on the spectra, one can eliminate this part of the corresponding A-scan by convoluting with a kernel that has a Fourier transform that is 1 for most of the z>0 axis, and 0 for most of the z<0 axis. An example of such a kernel is (−i/4, ½, +i/4). Convolution with a short kernel such as this one is more efficient than computing the Fourier transform; the convolution operation could be seen as an efficient approximation to the Hilbert transform. The resulting fringe spectra are complex valued and have a Fourier transform that is largely attenuated along the range z<0. After performing this convolution, the cross-correlation can be computed as above.

Thus an efficient method to obtain the integrated squared magnitude of the cross-correlation between two A-scans, using only the two spectra comprising the SD-OCT measurements of two A-scans, is as follows: 1) Isolate the fringe part of the spectra by subtracting the reference beam. 2) Perform an approximate Hilbert transform on each spectrum, for example by convolution with the truncated kernel described in the paragraph above. 3) Form the sums of the pointwise products of pairs of transformed spectra, to obtain cross-correlations $C_{12}$.

An extension of this fast cross-correlation technique provides an alternative method to estimate the sample displacement along z. The cross-correlation has a peak at a position corresponding to the motion along z, and the magnitude of the cross-correlation is symmetric about that peak. Therefore an estimate of the motion can be extracted by computing the average value of z, weighted by the squared magnitude of the cross-correlation:

$$\Delta z = \frac{1}{C_{12}} \int z \cdot |X_{12}(z)|^2 dz$$
$$= \frac{1}{C_{12}} \int S_1^*(q) S_2(q) \frac{1}{2i} \frac{d}{dq} [S_1(q) S_2^*(q)] dq \Big/ \sqrt{\int S_1^2 dq \cdot \int S_2^2 dq}$$

The longitudinal displacement is given by $\Delta z$ calculated by the formula above, instead of by searching the function $X_{12}(t)$ for its peak value.

This method allows several variations and extensions. The scan pattern collecting the main OCT image need not be a raster scan, but can be any set of A-scans that build a useful OCT data set. This method is useful so long as a set of guidepost A-scans can be acquired in locations that are likely to be included in the full OCT data set, given expected motion of the sample. The set of A-scans serving as guideposts can be acquired before or after the main OCT image. The comparison function need not be a cross-correlation, but can by any measure of the likelihood that two A-scans have measured the same location on the sample. Some alternate methods to compare candidate pairs of A-scans are: their mean-square difference, their Kullback Leibler distance, or the mutual information metric between the candidate pair. The comparison method can be applied to OCT optical scattering data in which the phase of the scattering is preserved, to OCT optical scattering data reduced to an intensity, or to logarithmically scaled intensities. Methods to reduce random noise in OCT data, such as thresholding and median filtering, have been described in the art and can be applied to the OCT data before comparison.

Although various embodiments that incorporate the teachings of the present invention have been shown and described in detail herein, those skilled in the art can readily devise many other varied embodiments that still incorporate these teachings.

The following references are hereby incorporated herein by reference.

US PATENT DOCUMENTS

Application US20050140984 Hitzenberger. "Efficient optical coherence tomography (OCT) system and method for rapid imaging in three dimensions"
U.S. Pat. No. 6,736,508 Xie, Kohnle, and Wei. "Tracking assisted optical procedure"
U.S. Pat. No. 4,937,526 Ehman and Felmlee. "Adaptive Method for Reducing Motion and Flow Artifacts in NMR Images"
Co-pending U.S. patent application Ser. No. 10/750,341, Hitzenberger, P. "Efficient optical coherence tomography (OCT) system and method for rapid imaging in three dimensions"
US20030199769, Podoleanu, A. et al. (2002) "Apparatus for high resolution imaging of moving organs" (WO03086181)

OTHER PUBLICATIONS

Ehman, R. L., and Felmlee, J. P. (1989) "Adaptive Technique for high-Definition MR Imaging of Moving Structures" *Radiology* 173(1): 255-263
Hammer, D. X., et al. (2005). *Journal of Biomedical Optics* 10(2): 0240380-1
Joergensen, T. M., et al. (2004) in "Coherence Domain Optical Methods and Optical Coherence Tomography in Biomedicine VIII" *Proceedings of SPIE* 5316: 204
Hitzenberger, C. K. et al. (2003). "Three-dimensional imaging of the human retina by high-speed optical coherence tomography." *Optics Express* 11(21): 2753-2761
Huang, D., E. A. Swanson, et al. (1991). *Science* 254 (5035): 1178-81
de Boer, J. F. et al. (2003) *Optics Letters* 28: 2067-2069
Choma, M. A., and M. V. Sarunic (2003) *Optics Express* 11: 2183-2189
Leitgeb, R. A., et al. (2003) *Optics Express* 11(8): 889-894
Nassif, N. A., B. Cense, et al. (2004). *Optics Express* 12(3): 367-376

What is claimed is:

1. A method for correcting the coordinates of longitudinal optical scattering profiles obtained from within a sample by an optical coherence tomography (OCT) imager, wherein the correction compensates for relative movement between the OCT system and the sample, said method comprising the steps of:
   acquiring a first set of longitudinal scans at a first plurality of transverse locations within the sample, said first period of scans all being taken during a first time period;
   acquiring a second set of longitudinal scans at a second plurality of transverse locations across the sample, said second plurality of scans being larger than the first plurality and said second set of scans all being taken during a second time period longer than said first time period and wherein at least some of the second plurality of transverse locations are close to at least some of the first plurality of transverse locations on the sample;
   matching certain ones of said second plurality of scans to certain ones of said first plurality of scans to define matched pairs, said matching being based on an evaluation of whether the associated optical scattering profiles of the scans are substantially similar;
   determining a displacement between coordinates associated with each of said matched pairs; and
   adjusting the coordinates associated with at least some of the scans of the second set based on the determined displacements thereby correcting for inaccuracies created by said relative movement during the acquisition of the second set of scans.

2. A method as recited in claim 1, wherein the displacement is determined along the longitudinal direction of the scan.

3. A method as recited in claim 1, wherein the transverse displacement is determined.

4. A method as recited in claim 1, wherein both the longitudinal and transverse displacements are determined.

5. A method as recited in claim 1, further comprising the step of generating an image using the optical scattering profile of the second set of scans and the adjusted coordinates associated therewith.

6. A method as recited in claim 1, wherein said first set of scans is acquired during a period short enough so that said relative movement is less than the amount that would cause objectionable image distortion.

7. A method as recited in claim 1, wherein the transverse locations of the second set of scans are in a two dimensional pattern.

8. A method as recited in claim 1, wherein the second set of scans is a raster scan.

9. A method as recited in claim 1, wherein the first set of scans is acquired temporally before the second set of scans.

10. A method as recited in claim 9, wherein the matching step and the displacement determining step are performed for some scans in the second set before all scans in the second set are acquired and further comprising the step of using some of the determined displacements to adjust the transverse locations at which some of the longitudinal scans in the second set are acquired.

11. A method as recited in claim 1, wherein the second set of scans is acquired temporally before the first set of scans.

12. A method as recited in claim 1, wherein the first time period is less than 200 milliseconds.

13. A method for correcting the coordinates of longitudinal optical scattering profiles obtained from within a sample by an optical coherence tomography (OCT) imager, wherein the correction compensates for relative movement between the OCT system and the sample, said method comprising the steps of:
   acquiring a first set of longitudinal scans at a first plurality of transverse locations within the sample;
   acquiring a second set of longitudinal scans at a second plurality of transverse locations in a two-dimensional pattern within the sample, wherein at least some of the second plurality of transverse locations on the sample correspond to at least some of the first plurality of transverse locations in the sample;
   matching certain ones of said second plurality of scans to certain ones of said first plurality of scans to define matched pairs, said matching being based on an evaluation of whether the associated optical scattering profiles of the scans are substantially similar;
   determining a displacement between coordinates associated with each of said matched pairs; and
   adjusting the coordinates associated with at least some of the scans of the second set based on the determined displacements thereby correcting for inaccuracies created by said relative movement during the acquisition of the second set of scans.

14. A method as recited in claim 13, wherein the displacement is determined along the longitudinal direction of the scan.

15. A method as recited in claim 13, wherein the transverse displacement is determined.

16. A method as recited in claim 13, wherein both the longitudinal and transverse displacements are determined.

17. A method as recited in claim 13, wherein the number of scans in the second set of scans is larger than the number of scans in the first set of scans.

18. A method as recited in claim 13, further comprising the step of generating an image using the optical scattering profile of the second set of scans and the adjusted coordinates associated therewith.

19. A method as recited in claim 13, wherein said first set of scans is acquired during a period short enough so that relative movement is less than the amount that would cause objectionable image distortion.

20. A method as recited in claim 13, wherein the first set of scans is acquired temporally before the second set of scans.

21. A method as recited in claim 20, wherein the matching step and the displacement determining step are performed for some scans in the second set before all scans in the second set are acquired and further comprising the step of using some of the determined displacements to adjust the transverse locations at which some of the longitudinal scans in the second set are acquired.

22. A method as recited in claim 13, wherein the second set of scans is acquired temporally before the first set of scans.

23. A method as recited in claim 13, wherein the first time period is less than 200 milliseconds.

24. A method as recited in claim 13, wherein the second set of scans is a raster scan.

25. A method of correcting for movement of the eye that occurs during the collection of data using an optical coherence tomography system, the method comprising:
   acquiring a first set of A-scans over a region of interest of the eye, said first set having a first resolution and being obtained during a first time period;
   acquiring a second set of A-scans of the region of interest, said second set having a second resolution, said second resolution being higher than the first resolution and being obtained over a second time period longer than the first time period;
   comparing A-scans in the first set to A-scans in the second set to find substantially matching pairs;
   analyzing the matched pairs to determine eye movement; and
   adjusting the originally assigned coordinates of the second set of A-scans based on the determined eye movement.

26. A method as recited in claim 25 wherein the second set of A-scans are acquired in a raster pattern and wherein the first set of A-scans is taken along a line diagonal to the raster pattern.

27. A method as recited in claim 25, further comprising the step of generating an image using the second set of A-scans after the adjustment step is performed.

28. A method as recited in claim 25, wherein the first set of A-scans is acquired temporally before the second set of A-scans.

29. A method as recited in claim 25 wherein the extent of the shift between the matched A-scans along the axis of the scan corresponds to the extent of eye movement along that axis.

30. A method as recited in claim 25 wherein eye movement perpendicular to the axis of the A-scans is determined by analyzing which of the A-scans in the first set matched an A-scan in the second set and calculating the difference of the coordinates therebetween.

31. A method as recited in claim 25 wherein the A-scans in the first set are compared to the to A-scans in the second by computing the cross-correlation between pairs.

32. A method of correcting for movement of the eye that occurs during the collection of data using an optical coherence tomography system, the method comprising:
   acquiring a first set of A-scans over a region of interest of the eye, said first set having a first resolution and being obtained during a first time period;
   acquiring a second set of A-scans of the region of interest, said second set having a second resolution, said second resolution being higher than the first resolution and being obtained over a second time period longer than the first time period;
   comparing A-scans in the first set to A-scans in the second set to find substantially matching pairs by computing the cross-correlation between pairs;
   analyzing the axial shift between the matched pairs to determine eye movement along the axis of the A-scan and determining eye movement perpendicular to the axis of the A-scan by analyzing which of the A-scans in the first set matched an A-scan in the second set and determining the displacement of the coordinates therebetween; and
   adjusting the originally assigned coordinates of the second set of A-scans based on the determined eye movement.

33. A method as recited in claim 32 wherein the second set of A-scans are acquired in a raster pattern and wherein the first set of A-scans is taken along a line diagonal to the raster pattern.

34. A method as recited in claim 32, further comprising the step of generating an image using the second set of A-scans after the adjustment step is performed.

35. A method as recited in claim 32, wherein the first set of A-scans is acquired temporally before the second set of A-scans.

* * * * *

UNITED STATES PATENT AND TRADEMARK OFFICE
CERTIFICATE OF CORRECTION

Page 1 of 1

PATENT NO. : 8,115,935 B2
APPLICATION NO. : 12/794926
DATED : February 14, 2012
INVENTOR(S) : Matthew J. Everett et al.

It is certified that error appears in the above-identified patent and that said Letters Patent is hereby corrected as shown below:

On page 2, under "OTHER PUBLICATIONS", in column 2, line 1, delete "clinocal" and insert -- clinical --, therefor.

On page 2, under "OTHER PUBLICATIONS", in column 2, line 2, delete "cohernce" and insert -- coherence --, therefor.

On page 2, under "OTHER PUBLICATIONS", in column 2, line 2, delete "sytems" and insert -- systems --, therefor.

On page 2, under "OTHER PUBLICATIONS", in column 2, line 24, delete "optial" and insert -- optical --, therefor.

In column 12, line 17, In claim 31, delete "to the to" and insert -- to the --, therefor.

Signed and Sealed this
Second Day of October, 2012

David J. Kappos
*Director of the United States Patent and Trademark Office*